United States Patent [19]

Blackstone

[11] Patent Number: 4,543,947
[45] Date of Patent: * Oct. 1, 1985

[54] CERVICAL SPINE COLLAR

[76] Inventor: Ralf W. Blackstone, 4678 Barker Way, Long Beach, Calif. 90814

[*] Notice: The portion of the term of this patent subsequent to Aug. 30, 2000 has been disclaimed.

[21] Appl. No.: 524,849

[22] Filed: Aug. 19, 1983

Related U.S. Application Data

[63] Continuation-in-part of Ser. No. 201,425, Oct. 28, 1980, Pat. No. 4,401,111.

[51] Int. Cl.4 ............................................. A61H 1/02
[52] U.S. Cl. .............................. 128/75; 128/DIG. 23
[58] Field of Search .................. 128/75, DIG. 23, 346

[56] References Cited

U.S. PATENT DOCUMENTS

| | | | |
|---|---|---|---|
| 2,102,069 | 12/1937 | Hanicke | 128/75 X |
| 2,818,063 | 12/1957 | Smith et al. | 128/DIG. 23 |
| 3,147,754 | 9/1964 | Koessler | 128/346 |
| 3,155,096 | 11/1964 | Outwin | 128/346 |
| 3,306,284 | 2/1967 | McKinley | 128/75 |
| 3,364,926 | 1/1968 | Alderson | 128/75 |
| 3,850,164 | 11/1974 | Hare | 128/DIG. 23 X |
| 4,205,667 | 6/1980 | Gaylord, Jr. | 128/75 |
| 4,401,111 | 8/1983 | Blackstone | 128/DIG. 23 X |

Primary Examiner—Richard J. Apley
Assistant Examiner—A. W. Cannon
Attorney, Agent, or Firm—Gunn, Lee & Jackson

[57] ABSTRACT

An improved cervical spine collar which takes the anatomy of the patient's lower head and upper torso into account comprising a rear section, left and right pliable sections, left and right side sections, left and right adaptation grooves, and left and right front sections. The rear section has an extension block and upper and lower comfort edges. The pliable sections permit the collar to bend to fit about the patient's neck and head. The side sections are sufficiently rigid to prevent lateral flexion and have support fins for support and comfort. The front sections collectively comprise a mandible buttress to block flexion and have a shoulder support, chin rotation blocks and cricochyrodectomy passage which may be used without obstructing placement, use or removal of the collar. The collar may be adjusted to fit various neck sizes through the use of optional side adjustments and inflatable tubes.

22 Claims, 10 Drawing Figures

CERVICAL SPINE COLLAR

BACKGROUND OF THE INVENTION

This application is a continuation-in-part of U.S. patent application Ser. No. 201,425 filed Oct. 28, 1980, now U.S. Pat. No. 4,401,111, having the same inventor and which is hereby incorporated by reference.

In accidents involving possible injury or fractures to the cervical spine, it is important to stablize the cervical spine as soon as possible. Movement of victims with cervical spine injuries often causes additional cervical injury, spinal cord trauma and paralysis. Flexive movement of the cervical spine is especially dangerous as 80–90% of spinal cord injuries occuring after the initial cervical spine injury are associated with this movement. The cervical spine collar of the present invention provides emergency stabilization of the cervical spine of a victim at the scene of an accident or trauma prior to moving the victim. The invention cervical spine collar positions the cervical spine in the range of 0 to 15 degrees of extension with a distracting force equal to the weight of the head or any portion thereof. In this position, pressure is taken off the fractured cervical vertebra and the head is arrested from movements which might drive fractured cervical vertebra bone fragments into the spinal cord.

While other cervical spinal collars exist, as set forth below, none are suited for emergency use as is the present invention. Further, none fully take into account the anatomy of the patient's head and upper torso in the designing of the means for stabilizing the neck. A commercial need has long existed, therefore, for a collar as described herein.

MATERIAL INFORMATION DISCLOSURE STATEMENT

Several cervical collars utilized in instances of possible cervical spinal injuries are known in the prior art. The following patents are related to the subject matter hereof but do not teach or suggest the present invention.

The cervical collar described in U.S. Pat. No. 3,285,244 to G. W. Cottrell comprises an adjustable member that encircles the neck of the wearer with a second member pivotally secured to the adjustable neck piece, the upper and lower edges of the cervical collar having inflatable pneumatic casings, the inflatable casings providing a means to apply variable traction on the cervical spine in accordance to the degree inflation of the casing. The Cottrell collar is not adapted for emergency use, does not properly support the head in the proper angle for maximum safety and realignment of slightly displaced vertebrae or fragments and is further not adaptable for application upon a patient at a predetermined distracting force upon the cervical spine.

U.S. Pat. No. 3,164,151 to E. D. Vere Nicoll, an inflatable splint to be used as an inflatable surgical collar or neck brace, comprises a plurality of vertically oriented tubular columns of air in communication with each other than when inflated around the neck of an injured person provide adequate support to an injured neck and head of the victim. A depression that receives the chin of the wearer in the inflatable splint tends to prevent and restrain rotational movement of the head of the victim. The Nicoll collar is extremely limited in its vertical adaptability and may only be used upon a single body size and type if the proper distraction force and angle of extension are to be obtained. Since an ambulance would not only have to maintain many such Nicoll collars, but the attendants would also have to instantly select the correct size collar upon pain of causing further spinal injury, the Nicoll collar is inadequate for use as an emergency cervical spine stabilization device.

The inflatable cervical collar disclosed in U.S. Pat. No. 3,765,412 to Ayub K. Ommaya, et al, is adapted to be worn by occupant of a motor vehicle. The cervical collar has a source of compressed gas connected to it, as well as triggering means associated with the compressed gas source. When the collar is inflated, such as in the case of a rear end collision, rotation of the head of the wearer of the collar is reduced or prohibited thus preventing a whiplash-like head or neck injury. Failure to provide the steadying support of a vertically inflexible superstructure as is shown in the invention cervical spine collar prevents stabilization of the neck in the secure manner or in the proper angle of extension as is required for proper emergency care. The cervical collar of the Ommaya, et al patent is therefore a preventive device unsuited to emergency use after cervical spine injury as in the case of the invention cervical spine collar.

Another inflatable cervical collar is disclosed in U.S. Pat. No. 3,343,532 to G. Zumaglini. The Zumaglini collar comprises a semi-rigid case of synthetic resin having a bottom portion adapted to bear on the clavicular region of a victim, a middle portion encircling the neck of a victim, and a top portion provided with rests for the sub-mandibular and occipital regions. In order to fit the cervical collar on a victim, the semi-rigid case is slotted on one side, the facing edges of the slot being provided with a closure, such as a sliding clasp fastener. The Zumaglini cervical collar is used as an alternative to the Styker frame bed and Crutchfield tongs in long-term treatment where full immobilization of the cervical rachis, traction and extension of a permanent character are desired. It further has such a high profile as to make it extremely dangerous to an unconscious cervically injured victim due to the displacement of the neck necessary to secure the collar. Additionally the Zumaglini collar is inappropriate for use in emergency situations because the side attachment upon which the collar relies prevents the crucial lateral cervical spine x-ray from being taken while the neck is secured within the collar.

SUMMARY OF THE INVENTION

An improved cervical spine collar which is designed to take the anatomy of the patient's head and upper torso into account comprising a rear section, left and right pliable sections, left and right side sections, left and right adaptation grooves, and left and right front sections. The rear section has an extension block and upper and lower comfort edges. The pliable sections and adaptation grooves permit the collar to bend to fit about the patient's neck. The side sections are sufficiently rigid to prevent lateral flexion and have support fins for support and comfort. The front sections collectively comprise a mandible buttress to block flexion and have a shoulder flange, chin rotation blocks and crico-chyrodectomy passage which may be used without obstructing placement, use or removal of the collar. The collar may be adjusted to fit various neck sizes through the use of optional side adjustments and inflatable tubes.

It is an object of the present invention to provide an improved cervical spine collar to be utilized in emergency stabilization of the traumatized cervical spine. The cervical spine collar when in position on an injured person holds the injured person's head in approximately 15 degree extension and distracts the head at a predetermined proper force to relieve pressure on the spine, prevent further injury to the cervical spine and use the paraspinous muscles and ligaments to realign any displaced vertebrae or fragments thus relieving pressure from the spinal cord.

Another object of the invention is to provide a universal collar which will be useable in diverse circumstances and which is sufficiently inexpensive to be widely distributed and sufficiently simple to be correctly used.

Further advantages and objects will be apparent to those knowledgeable in the art.

DESCRIPTION OF THE PREFERRED EMBODIMENT

Figure 1:
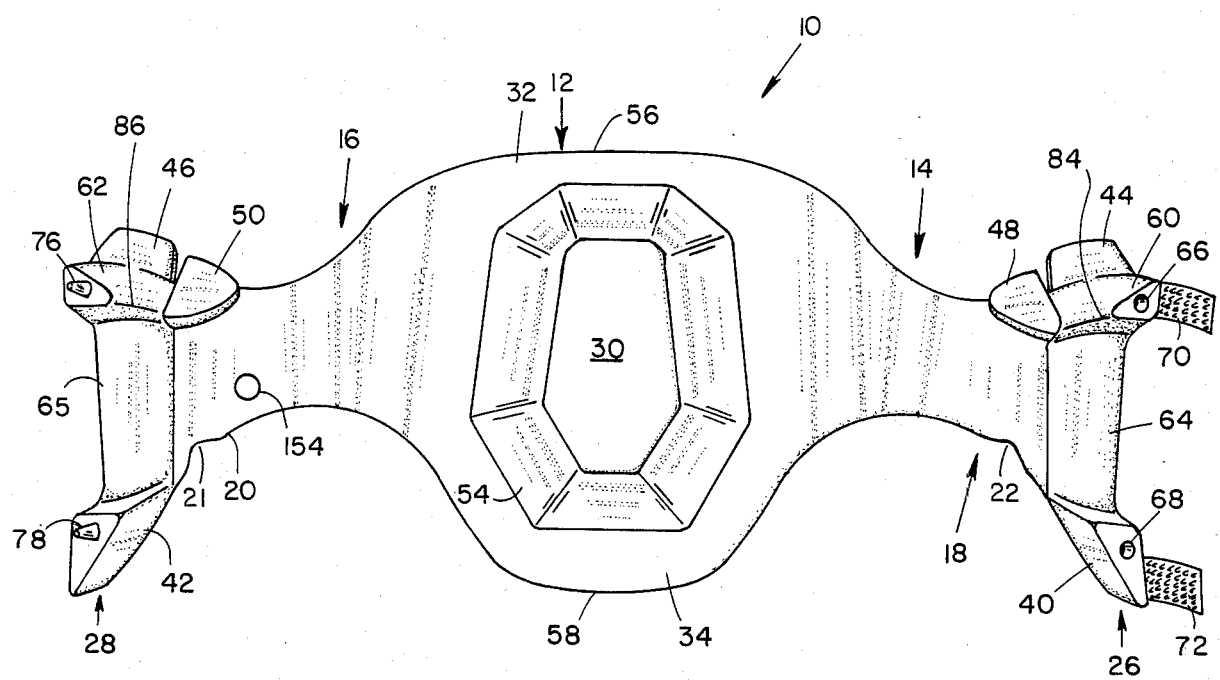
FIG. 1 is an illustration of one embodiment of the invention.
Figure 2:
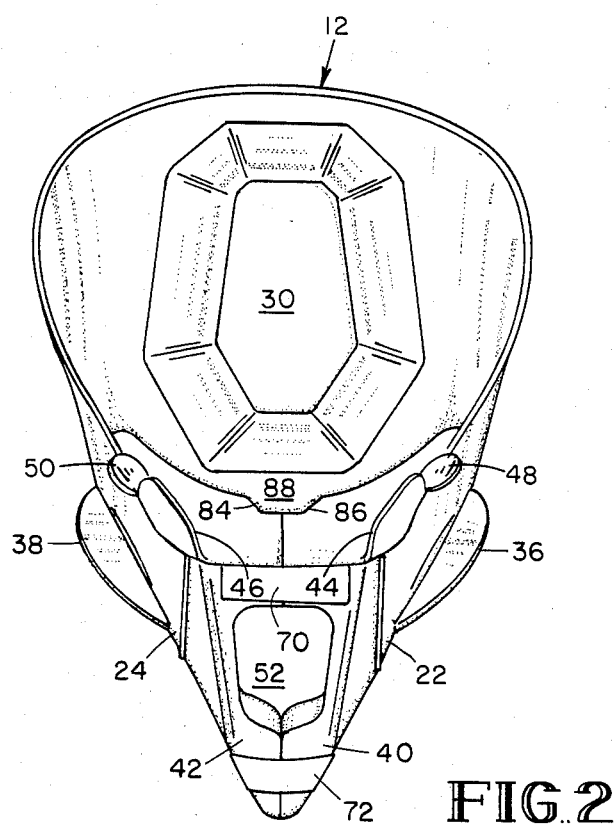
FIG. 2 is an illustration of the collar of FIG. 1 as it appears when closed.
Figure 3:
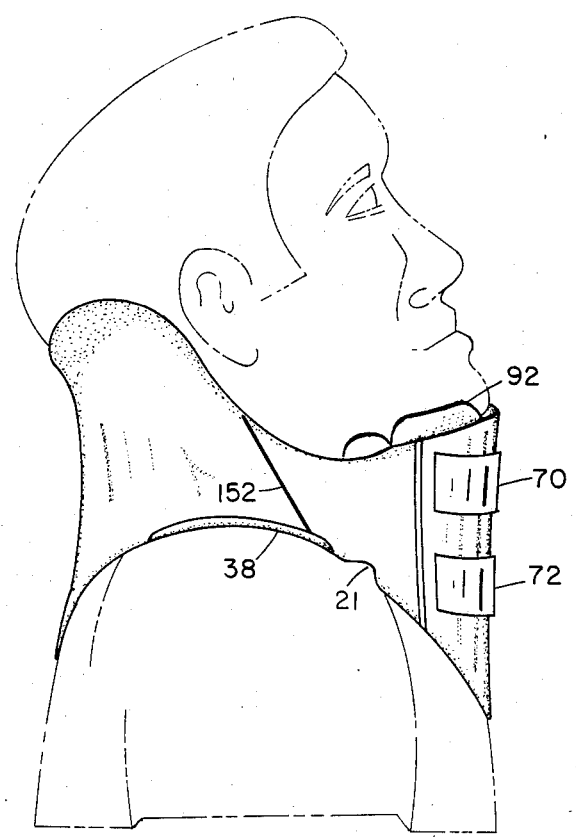
FIG. 3 is a side view of the collar of FIG. 1 in place about a patient's neck.

FIGS. 1, 2 and 3 show the improved cervical spine collar 10 comprising a rear section 12, left and right pliable sections 14 and 16, left and right side sections 18 and 20, left and right adaptation grooves 22 and 24, and left and right front sections 26 and 28. The rear section has an extension block 30 and upper and lower comfort edges 32 and 34. The pliable sections 16 and 18 permit the collar to bend to fit about the patient's neck. The side sections 18 and 20 are sufficiently rigid to prevent lateral flexion and have support fins 36 and 38 for support and comfort. The front sections 26 and 28 collectively have mandible buttresses 60 and 62 and manubriosternal buttresses 40 and 42, to block flexion of the head and neck, chin rotation blocks 44 and 46, mandible comfort pads 48 and 50 to prevent lateral rotation of the head and neck and, a cricothyrotomy passage 52 which may be used without obstructing placement, use or removal of the collar 10.

The collar 10 is substantially flat and adapted to be placed about the neck of the patient suspected of cervical spine injury with a minimum of movement of said patient and is adapted to fit closely about and conform to the patient's lower head and upper torso when fastened about said neck to comfortably prevent substantial flexion, extension or lateral flexion.

Figure 7:
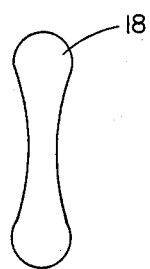
FIG. 7 is a side view of a side section of the collar showing its self bracing construction.

The collar 10 is designed to be composed of a single unit made of a single affordable material and to be easily manufacturable. These qualities assist in making the collar sufficiently inexpensive to be widely distributed throughout all emergency medical units and reduces the possibility of failure on the part of the collar due to disjunction of parts of the collar 10. The single material should be both rigid enough to hold a victim's head in a fixed position to prevent flexion and extension of the neck and flexible enough to be longitudinally wrapped by a paramedic or ambulance attendant about the victim's neck without moving the victim after sliding the flat collar beneath the victim's neck. It has been found that the preferred material is a molded, high density rubber or skinned plastic foam. These materials are treated to cause the outer foam cells to collapse thus forming a hard plastic skin approximately one millimeter or less thick. As shown in FIG. 7 the side sections 18 and 20 may be formed to slightly bow inward for the purpose of causing vertical pressure to compress the side sections 18 and 20 by bowing them further inward and thus increasing their vertical firmness.

The materials chosen to comprise the collars are radiolucent to permit even soft tissue radiographs.

The extension block 30 is preferrably approximately one half inch thick at its thickest point plus one half inch or minus one quarter inch depending upon the materials used and the size collar made. Use of other materials will permit a wider variation in the allowed thickness. The dimensions of the extension block 30 are designed to allow it to rigidly fit between the back of the head and the upper portion of the back to prevent extension of the head and neck. The extension block 30 is surrounded on the inner side of the collar 10 by an extension block shoulder 54 in the shape as shown in FIG. 1. The extension block shoulder 54 slopes down about the extension block 30 to the upper and lower comfort edges 32 and 34 and to the left and right pliable sections 14 and 16. The slope of the decreasing thickness of the collar 10 decreases where the extension block shoulder 54 meets the upper and lower comfort edges 32 and 34 and left and right pliable sections 14 and 16. The thickness of the upper and lower comfort edges 32 and 34 gradually decreases going away from the extension block 30 until they have a thickness of approximately one-sixteenth of an inch at the upper and lower collar edges 56 and 58. The slope of the extension block shoulder 54 conforms to the angles of the back of the victim's head and the upper back area which are braced by the extension block 30. The comfort edges 32 and 34 further spread the rearward pressure from the extension block shoulder 54 over greater portions of the victim's head and upper back to stabilize and support the collar 10 and to ease the patient's discomfort.

The left and right pliable sections 14 and 16 are preferably approximately one-sixteenth of an inch thick, much thinner than either the extension block 30 or left and right side sections 18 and 20. When the collar 10 is placed next to the victim's neck, therefore, and the left and right side sections 18 and 22 are gently raised, the collar 10 preferentially bends at the left and right pliable sections 14 and 16 without requiring undue effort or extreme measures to stabilize the victim's head.

Also joining the rear section 12 to the left and right side sections 18 and 20 are left and right support fins 36 and 38 which are attached to the outer sides of the left and right pliable sections 14 and 16 and which continue in each direction to connect the rear section 12 to the left and right side sections 18 and 20 as shown in FIG. 2. The support fins 36 and 38 extend approximately 1 inch from the collar 10, are approximately one-fourth inch thick at their bases where they are attached to the collar 10 and approximately one-sixteenth of an inch at the outer edge. The support fins 36 and 38 and pliable sections 14 and 16 are curved to closely fit about the patient's shoulders to more evenly spread the weight of the head over the sensitive shoulder and collar bone area and to assist in preventing lateral flexion of the collar 10.

Left and right side sections 18 and 20 are approximately one-fourth of an inch thick and are sufficiently rigid to prevent flexion by the victim's head and neck.

Left and right sizing ridges 22 and 24 are narrow ridges. After the rear section 12 of the collar 10 has been placed behind the victim's neck and head and the side sections 18 and 20 bent to either side of the victim's neck and the left and right front sections 26 and 28 are pushed in towards each other in front of the victim's head to meet between the victim's head and sternum to form the unit shown in FIG. 2 positioned as shown in FIG. 3. These are sizing grooves or ridges and binding should not occur at these points.

Left front section 26 is comprised of left front mandible buttress 60, chin rotation block 44 chin comfort pad 48, left center support 64, sternal support 40 and registration recesses 66 and 68. Male velcro fasteners 70 and 72 are located upon the outer surface of left front section 22.

Right front section 26 is comprised of right front mandible buttress 62, chin roation block 46, chin comfort pad 50, right center support 66, sternal support 42 and registration protrusions 76 and 78. Female velcro fasteners 80 and 82 (not shown) are located upon the outer surface of left front section 20.

The general configuration of the collar 10 and of the front sections 26 and 28 in particular is designed to hold the patient's head and neck in a range of 0° to 15° angle of extension, an angle which has been found to align the paraspinous muscles and ligaments and often realign many slightly displaced vertebrae or vertebrae fragments.

The combination of registration recesses 66 and 68 and protrusions 76 and 78 together with the velcro fastener combinations permit rapid placement and securing of the collar 10 about the victim in a manner which effectively welds it into a single solid unit.

The front sections 26 and 28 cradle and immobilize the distal chin and anterior neck of the sternum. Chin comfort pads 48 and 50 are inwardly curved plate members attached to side sections 18 and 20 respectively in a manner which permits them to pivot as the collar is applied about the victim's mandible. This creates a comfortable but secure fit. Because chin comfort pads 48 and 50 are not attached to the mandible buttress as are chin rotation blocks 44 and 46 they curve about the chin to a greater extent than chin rotation blocks 44 and 48 which rigidly hold the chin in place and prevent chin rotation.

The mandible buttresses 60 and 62 each contain inner notches 84 and 86 which, when the collar is fastened form chin recess 88 as shown in FIG. 2. Chin recess 88 solves the prior art problem of pinching the patient's lower chin between the left and right mandible buttresses 60 and 62 when the collar 10 was affixed about the patient's head and neck.

The cricothyrotomy passage 52 is formed between the front sections 26 and 28 as shown in FIG. 2. Because of the location of the support structure preventing flexion of the head and neck about the cricothyrotomy passage 52 in combination with the location of the opening means of the collar 10 running through the cricothyrotomy passage 52 an emergency cricothyrotomy may be performed on the patient prior to or subsequent to placement of the collar 10 about the patient's head and neck and the patient's carotid pulse checked at any time through this same said passage. A preferable size for the passage is approximately 4"×1.5".

Comfort edge 34 extends slightly below the level of the shoulders and the front sections 26 and 28 buttresses the chin directly off of the patient's manubriosternal junction of the sternum. This corrects a problem of some prior art collars which did not extend below the shoulder level in the rear and either did not buttress directly off the manubriosternal junction at all or only did so secondarily. Such prior collars were, therefore, inherently either unstable due to lack of support from an immovable front body member or uncomfortable due to the great pressure used to maintain stability. Rear extension of the collar 10 and buttressing directly off the manubriosternal junction prevents these problems. Further, it has been found that with the head distracted at the proper angle of extension, approximately 15°, and with the proper amount of force, the paraspinous muscles and ligaments of the victim relign any slightly displaced vertebrae or fragments and pressure on the spinal cord is relieved.

Figure 4:
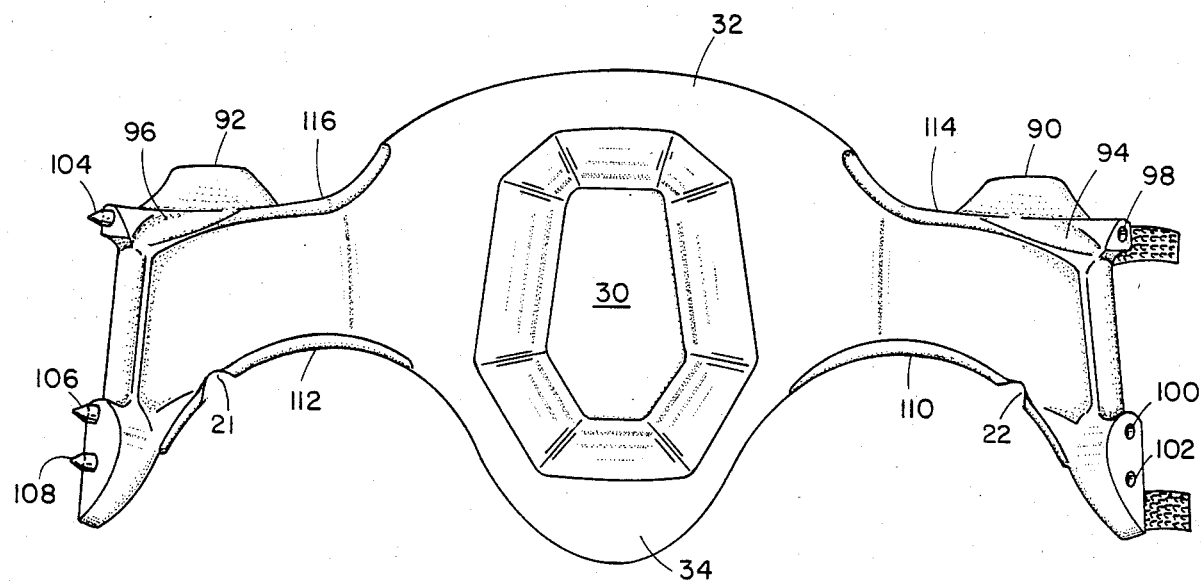
FIG. 4 is an illustration of another embodiment of the invention.

FIGS. 3 and 4 show an alternative means of preventing chin rotation due to use of a single chin rotation blocks 90 and 92 on each front section 26 and 28. The alternative chin rotation blocks 90 and 92 are shown in FIGS. 3 through 6.

Figure 6:
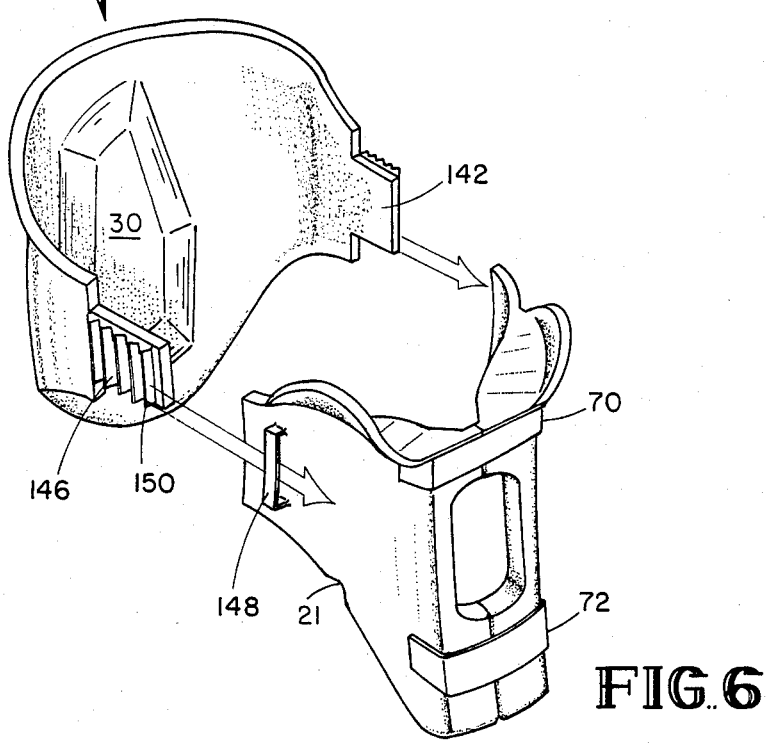
FIG. 6 is an illustration of another embodiment of the invention showing side adjustments.

An alternative chin slot can be comprised from the mandible hollows 94 and 96 as shown in FIG. 6. Additionally, the collar front stabilization and registration members may alternatively be designed and constructed as recesses 98, 100 and 102 and protrusions 104, 106 and 108 are shown in FIG. 4.

An alternative means of supporting the head's weight upon the collar bones and preventing lateral flexion is shown in FIG. 4. Lower side section reinforcements 110 and 12 comfortably spread the weight of the head over the shoulder while the clavical recesses prevent pressure on the collar bones.

A further alternative means of supporting the head's weight is to mold or otherwise attach ribs to the collar 10 for the purpose of adding vertical support and rigidity to the collar 10.

Figure 5:
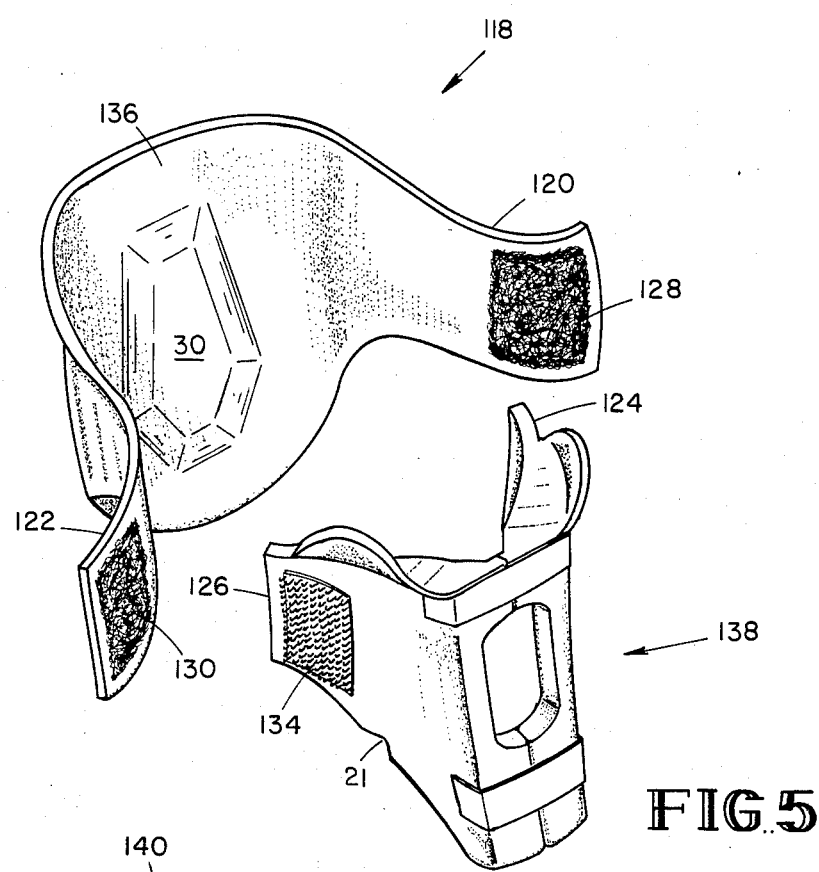
FIG. 5 is an illustration of another embodiment of the invention showing side adjustments.

Alternative means of providing emergency cervical collars capable of fitting a greater proportion of the population are shown in FIGS. 5 and 6.

The first universal collar 118 has extended rear side sections 120 and 122 which are capable of fitting about the patient's neck and overlapping forward side sections 124 and 126. The means of attaching the rear side sections to the forward side sections for the first universal collar 118 is through the use of female velcro strips 128 and 130 attached to the inner faces of rear side sections 120 and 122 respectively and male velcro patches 132 (not shown) and 134 attached to the outer faces of forward side sections 124 and 126 respectively. It is important to place the female or receiving portion of velcro upon the inner faces of rear side sections 120 and 122 to avoid scratching the neck of the patient.

To use first universal collar 118 the back portion 136 is slid behind the patient's neck and the forward portion 138 positioned between the patient's neck and sternum. When the desired extension of the neck, preferrably 15°, is achieved, the rear side sections 120 and 122 are tightly affixed to front side sections 124 and 126 by pressing female velcro patches 128 and 130 upon male velcro patches 132 and 134. The resulting collar combination securely prevents the patient's head from being moved relative to his torso. This collar is useful for units such as emergency vehicles which have only limited storage capacity and which are likely to need the invented cervical spinal collar upon an emergency basis. This type of collar also allows the exact fitting of persons with long neck length but small circumference.

Because the side sections 18 and 20 remain unchanged from collar 10 easy access to the neck is still achieveable via either the cricothyrotomy passage 52 or, if necessary, by opening the front of the collar by opening fasteners 70 and 80 and 72 and 82 and separating the side sections 18 and 20.

The second universal collar 140 shown in FIG. 6 functions in a manner similar to that of the first universal collar 118. Left adjustable tab 142 may be fitted into right adjustable tab holder 144 (not shown) and right adjustable tab 146 fitted within right adjustable tab holder 148 as shown in FIG. 6. The adjustable tabs are comprised of rows of triangular ridges 150 which, upon insertion into the adjustable tab holders 144 and 148 prevent the adjustable tabs 142 and 146 from being withdrawn. Thus second universal collar 140, when placed about the victim's head and neck in the manner as described for adjustable collar 118 also secures the patient from further spinal injury.

Figure 9:
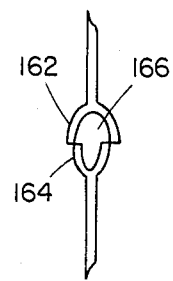
FIG. 9 is a cross sectional view of FIG. 8.
Figure 8:
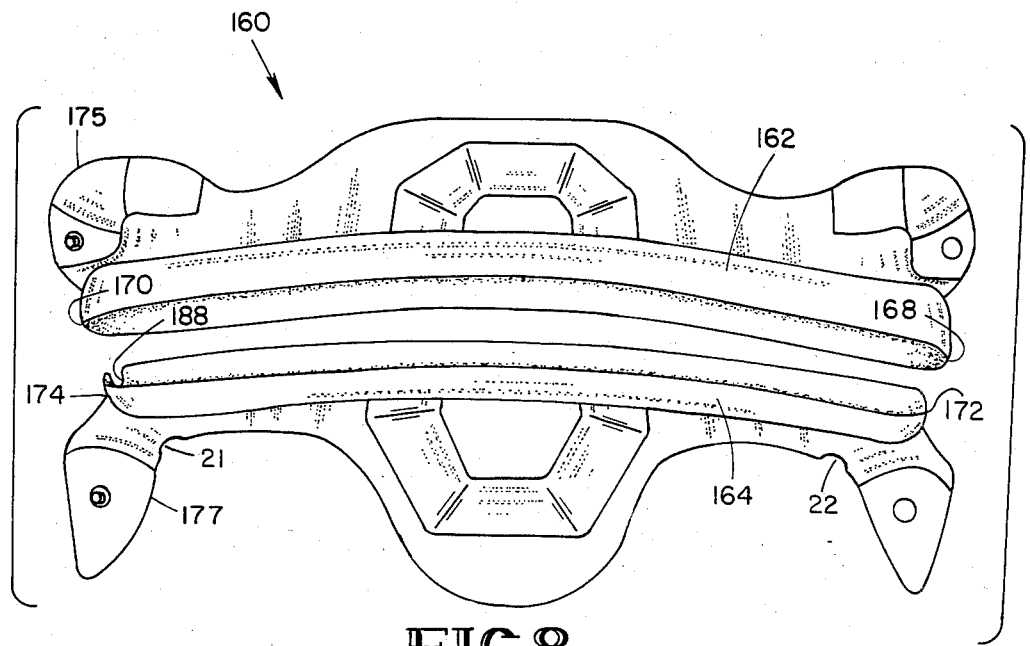
FIG. 8 is an illustration of another embodiment of the invention capable of vertical adjustment.
Figure 10:
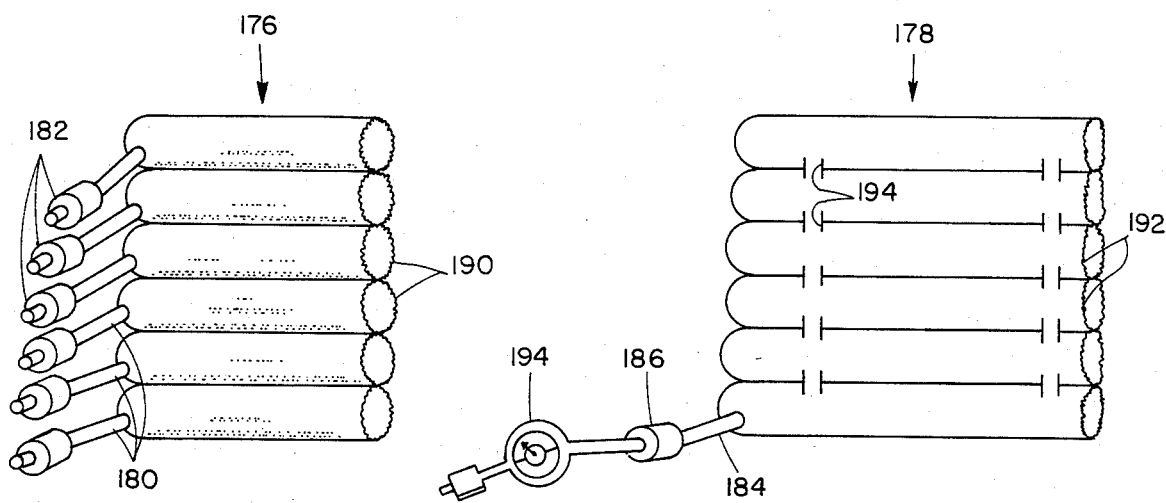
FIG. 10 is an illustration of alternative embodiments of the vertical adjustment means for use with the collar of FIG. 8.

The third universal collar 160 shown in FIG. 8 is vertically adjustable to accomodate persons having long or short necks or those with neurologic deficits requiring traction and stabilization. The superstructure of the third universal collar 160 is similar to that of collar 10 with the addition of longitudinally positioned upper and lower vertical adjustment troughs 162 and 164. The FIG. 9 cross sectional view of FIG. 8 shows that the sides of the lower vertical adjustment trough 164 fit within the sides of upper vertical adjustment trough 162 to form a vertically adjustable longitudinal cavity 166 along the entire length of third universal collar 160 until its upper ends 168 and 170 and lower ends 172 and 174 at either end of the third universal collar 160. The superstructure of rear, pliable, side and front sections is thereby divided between an upper superstructure 175 and a lower superstructure 176. Either the first or second vertical adjustment means 176 and 178 as shown in FIG. 10 may be enclosed within the longitudinal cavity 166. The multiple valve stems 180 and valves 182 of the first vertical adjustment means 176 or the single valve stem 184 and valve 186 of the second vertical adjustment means 178 protrude through slot 188 to outside the third universal collar 160.

The first vertical adjustment means is comprised of a multilumen balloon 190 of thin but tough plastic such as mylar which is sized to securely fit within the longitudinal cavity 166. Each lumen thereof is separately controlled by a single valve stem 180 and valve 182 pair to permit precisely controllable vertical adjustment of the third universal collar 160 when fitted within longitudinal cavity 166. Second vertical adjustment means 178 is comprised of several lumens 192 which interconnect through passages 194 to permit the filling and emptying of the several lumens 192 by a single valve stem 184 and valve 186 pair. Variations using multiple lumens, some of which are communicably connected and some of which are not and several valves may be used as desired. If a particular lateral flection angle is desired the lumens may be vertically separated, valve stems and valves placed on each end and the pressure within each side independently varied. An advantage of the first vertical adjustment means 176 is the ability of varying the collar height independent of traction due to the even vertical adjustments caused by completely filling one lumen 190 prior to filling the next. The second vertical adjustment means fills more easily but will differentially first fill those portions of the longitudinal sections under the least pressure rather than fill evenly, and cannot vary height independent of traction.

Use of a pressure gauge 194 to determine the pressure within the vertical adjustment means permits the third universal collar 160 to simply fit snuggly about the patient to prevent further injury or, with an increase in pressure, to place the patient's neck in precisely regulatable traction.

A variation of these designs is to build a separate longitudinal cavity of the type 166 into each of the three portions of the first or second universal collars 118 and 140 for the purpose of providing both vertical and horizontal adjustment means. A further variation is to construct the front sections 18 and 20 of the first and second universal collars 118 and 140 as a single unseparatable unit having a longitudinal tube therein for use in conjunction with a longitudinal tube in the rear section. The various separate longitudinal tubes would preferably be communicatively interconnected during inflation and deflation by means of at least one tube to maintain constant pressure throughout during adjustment of the collar. Thus a truly universal collar may be constructed using the principles and designs set forth herein.

To further the goal of producing a universal emergency collar another method is to attach inflatable tubes to either or both the inferior and superior surfaces of the collar 10. This would be preferably done with a tube comprised of multiple independently inflatable and regulatable lumens each fitted with its own stem and valve to permit greater control upon the amount of traction with which the neck is held. A less preferable but more convenient method would be to use only one or only a few valves to inflate and control the many lumens.

To facilitate the testing of the density of the collar 10 material small circles 154 or other indicators can be made a part of each collar 10 to insure that density testing is uniformly performed in precisely the same location for each collar 10 tested.

Either or both the inferior and superior surfaces of the collar 10 may be padded for greater comfort.

The invention is intended for short term immobilization of possible cervical spine fractures until x-rays rule out or confirm fracture of the spine and Crutchfield tongs and Stryker-frame bed or Halo apparatus may be deemed necessary. The features of total immobilization with sufficient anterior and posterior support to withstand great force to the head, proper angular extension of the head and properly balancing of the weight of the head to cause alleviation of pressure on the spinal cord, each of applying the collar without further injuring the victim, location of the closure mechanism out of the path of lateral diagnostic neck x-rays and anterior location of a neck access for access to the victim's respiratory tract are each novel to the invention cervical spine collar. The invention is also capable of being used for permanent or semipermanent applications.

For the purpose of descriptions herein it is understood that "upper", "lower", "vertical" and "horizontal" are used in reference to a collar worn by a patient standing straight up, that "longitudinal" refers to the long axis of the collar, that "latitude" refers to the short axis of the collar and that "thickness" refers to the measurement from the inside of the outside of the collar. "Extension" is motion of the head and neck towards the back, "flexion" is motion of the head and neck towards the sternum, "rotation" is motion of the head and neck in a plane parallel to the shoulders and "lateral flexion" is motion of the head and neck which brings them closer to either shoulder.

The fins 36 and 38 may also be placed upon the side sections 18 and 20 as shown in the collars of FIGS. 5 and 6.

It is apparent from the above description that signification improvements on the art of caring for victims of cervical spine trauma are achieved by the instant invention. While the invention has been described in connection with the preferred embodiment is not intended to limit the invention with the particular form set forth, but, on the contrary, it is intended to cover such alternatives, modifications and equivalence as may be included within the spirit and scope of the invention as defined by the appended claims.

I claim:

1. A cervical spine collar for providing cervical spine stabilization when placed about a patient's neck comprising:

an elongated superstructure comprised of a rear section, left and right pliable sections, left and right side sections and left and right front sections, and adapted to be placed about said patient's neck and fastened closely about said patient's lower head and upper torso to prevent substantial extension, flexion or lateral flexion;

said left and right front sections collectively being capable of preventing substantial flexion when said collar is fastened about said neck and each having a mandible buttress, a center support and a manubriosternal buttress which collectively define a cricothyrotomy passage sufficiently large to permit useful access to said patient's anterior throat even palpatation of carotid pulses;

said rear section designed to fit behind said patient's head and neck to prevent substantial extension and comprised of an extension block, an upper comfort edge and a lower comfort edge, said extension block being sufficiently vertically rigid to prevent extension, said upper comfort edge being sufficiently flexible to secure and accomodate nonlinear portions of the back of said head and said lower comfort edge being sufficiently flexible to secure and accomodate the nonlinear portions of said patient's upper back;

said left and right pliable sections connect to either end of said rear section respecitvely and are sufficiently flexible to permit said collar to bend preferentially at said pliable sections when bent about said neck and entrap the occipital tubercles of the skull to prevent lateral flexion and are curved upon their inferior surface to accomodate said patient's shoulders;

said left and right side sections connect said left and right pliable sections to said left and right front sections respectively;

left and right support fins attached to left and right pliable sections respectively, each support fin extending horizontally out from said collar over a collar bone of said patient and curved to accomodate said shoulder surfaces.

2. The collar of claim 1 wherein said left and right front sections may be reversably joined by fasteners located on said mandible buttresses and manubriosternal buttresses and reinforced with vertical alignment supports located on said mandible buttresses and manubriosteral buttresses and collectively buttress said patient's chin directly off said patient's maunbriosternal junction to prevent substantial flexion while permitting access to said neck via said cricothyrotomy passage and wherein said left and right front sections may be reversably separated to permit greater access to said anterior neck without removing said rear section.

3. The collar of claim 2 wherein said right and left mandible buttress collectively define a chin recess for facilitating placement of said collar about said neck without pinching said patient's lower chin or neck.

4. The collar of claim 2 wherein rotation is prevented by left and right chin rotation blocks located upon left and right mandible buttresses respectively and wherein chin comfort is facilitated by left and right chin comfort pads located upon left and right side sections respectively which comfort pads are pivotally attached to said side sections to permit said comfort pads to rotate during placement of said collar about said patient to create a comfortable and secure fit.

5. The collar of claim 2 wherein left and right upper supports are located upon the upper edges of said left and right pliable sections and said left and right side sections respectively to reinforce said pliable and side sections for preventing lateral flexion and for rounding the upper edges of said pliable and side sections for greater comfort.

6. The collar of claim 2 wherein said superstructure is a single unit comprised of a radiolucent plastic foam material having a smooth outer surface.

7. The collar of claim 2 wherein said collar is latitudinally reinforced with vertical ribs longitudinally spaced about said collar as needed to prevent latitudinal bending of said collar.

8. The collar of claim 2 wherein said collar is substantially flat when not in use and is capable of being placed about said patient's neck to effect range of 0° to 15° angle of extension at the scene of an injury to said patient's cervical spine with minimum movement of said patient by paramedical personnel.

9. The collar of claim 2 wherein said superstructure is longitudinally divided between an upper superstructure and a lower superstructure by a vertically adjustable longitudinal cavity located approximately midway along its entire length, said vertically adjustable longitudinal cavity containing a vertical adjustment means capable of affecting the height of said collar.

10. A universal emergency cervical spine collar for fitting patients of different sizes comprising;

a rear section designed to fit behind said patient's head and neck comprising an extension block, an upper comfort edge and a lower comfort edge, said extension block being sufficiently vertically rigid to prevent extension when said collar is fastened about said patient's neck, said upper comfort edge being sufficiently flexible to accomodate the back of said patient's head and said lower comfort edge being sufficiently flexible to accomodate said patient's upper back;

left and right front sections each having a mandible buttress, a center support and a manubriosteral buttress, and being capable of collectively preventing substantial flexion when said collar is fastened about said neck;

left and right chin rotation blocks located upon said left and right mandible buttresses respectively which are capable of preventing substantial rotation;

a cricothyrotomy passage sufficiently large to permit useful access to said patient's anterior throat located below said mandible buttresses, between said center supports and above said manubriosternal buttress;

left and right pliable sections connected to either end of said rear section which are sufficiently flexible to bend about said neck and entrap the occipital tubercles of the skull to prevent lateral flexion;

longitudinally adjustable left and right attachment means, left inner attachment means located upon the inner side of left pliable section and left outer attachment means located upon the outer side of left side section, right inner attachment means located upon the inner side of right pliable section and right outer attachment means located upon the outer side of right side section, said left inner and outer attachment means and said right inner and outer attachment being capable of securely attaching to each other enabling said collar to firmly fit said collar about more than one said neck size.

11. The collar of claim 10 wherein said left and right attachment means are velcro attachment means.

12. The collar of claim 10 wherein said left and right attachment means are rib and tab attachment means.

13. The collar of claim 10 wherein left and right support fins are attached to said left and right side sections respectively each said support fin extending horizontally out from said collar over the shoulder area of said patient and curved to accomodate said shoulder area.

14. The collar of claim 10 wherein said collar is capable of firmly positioning said patient's head and neck in an approximate 0° to 15° angle range of extension by attaching said longitudinally adjustable left and right attachment means to cause placement of said left and right front sections under said patient's chin to effect an approximate 0° to 15° angle range of extension and is capable of being placed about said patient's neck at the scene of an injury to said patient's cervical spine with minimum movement of said patient by paramedical personnel.

15. The collar of claim 10 wherein said left and right front section s may be reversibly joined by fasteners located on said mandible buttresses and clavical supports and reinforced with vertical alignment supports located on said mandible buttresses and clavical supports and collectively buttress said patient's chin directly off said patient's maunbriosternal junction to prevent substantial flexion while permitting access to said neck via said cricothydroidectomy passage and wherein said left and right front sections may be reversably separated to permit greater access to said anterior neck without removing said rear section.

16. The collar of claim 10 wherein said right and left mandible buttress collectively define a chin recess for facilitating placement of said collar about said neck without pinching said patient's lower chin or neck wherein rotation is prevented by left and right chin rotation blocks located upon left and right mandible buttresses respectively and wherein chin comfort is facilitated by left and right chin comfort pads located upon left and right side sections respectively which comfort pads are pivotally attached to said side sections to permit said comfort pads to rotate during placement of said collar about said patient to create a comfortable and secure fit and wherein said superstructure is a single unit comprised of a radiolucent plastic foam material.

17. The collar of claim 10 wherein said collar is longitudinally divided between an upper collar and a lower collar by a vertically adjustable longitudinal cavity located approximately midway along its entire length, said vertically adjustable longitudinal cavity containing a vertical adjustment means capable of affecting the height of said collar.

18. A cervical spine collar for providing cervical spine stabilization when placed about a patient's neck comprising:

an elongated superstructure longitudinally divided between an upper superstructure and a lower superstructure by a vertically adjustable longitudinal cavity located approximately midway along its entire length, said vertically adjustable longitudinal cavity containing a vertical adjustment means capable of affecting the height of said collar, said superstructure being comprised of a rear section, left and right pliable sections, left and right side sections and left and right front sections, and adapted to be placed about said patient's neck and fastened closely about said patient's lower head and upper torso to comfortably prevent substantial extension, flexion or lateral flexion with minimum of movement of said patient;

said left and right front sections collectively being capable of preventing substantial flexion when said collar is fastened about said neck and each having a mandible buttress, a center support and a manubriosternal buttress which collectively define a cricothyrotomy passage sufficiently large to permit useful access to said patient's anterior throat;

said rear section designed to fit behind said patient's head and neck to prevent substantial extension and comprised of an extension block, an upper comfort edge and a lower comfort edge, said extension block being sufficiently vertically rigid to prevent extension, said upper comfort edge being sufficiently flexible to secure and accomodate nonlinear portions of the back of said head and said lower comfort edge being sufficiently flexible to secure and accomodate the linear portions of said patient's upper back;

said left and right pliable sections connect to either end of said rear section respectively are sufficiently flexible to permit said collar to bend preferentially at said pliable sections when bent about said neck and are curved upon their inferior surface to accomodate said patient's collar bones to trap the occipital tubercles and prevent lateral flexion;

said left and right side sections connect said left and right pliable sections to said left and right front sections respectively.

19. The collar of claim 18 wherein left and right support fins are attached to left and right pliable sections respectively, each support fin extending horizontally out from said collar over a shoulder area of said patient and curved to accomodate said shoulder areas.

20. The collar of claim 18 wherein said connections between said left side section and left pliable section and right side section and right pliable section are comprised of longitudinally adjustable left and right attachment means respectively, left inner attachment means located upon the inner side of left pliable section and left outer attachment means located upon the outer side of left side section, right inner attachment means located upon the inner side of right pliable section and right outer attachment means located upon the outer side of right side section, said left inner and outer attachment means and said right inner and outer attachment capable of being securely attaching to each other enabling said collar to firmly fit said collar about more than one said neck size.

21. The collar of claim 18 wherein said left and right front sections may be reversably joined by fasteners located on said mandible buttresses and clavical supports and reinforced with vertical alignment supports located on said mandible buttresses and clavical supports and collectively buttress said patient's chin directly off said patient's manubriosternal junction to prevent substantial flexion while permitting access to said neck via said cricothyrotomy passage and wherein said left and right front sections may be reversably separated to permit greater access to said anterior neck without removing said rear section.

22. The collar of claim 18 wherein said right and left mandible buttress collectively define a chin recess for facilitating placement of said collar about said neck without pinching said patient's lower chin or neck wherein rotation is prevented by left and right chin rotation blocks located upon left and right mandible buttresses respectively and wherein chin comfort is facilitated by left and right chin comfort pads located upon left and right side sections respectively which comfort pads are pivotally attached to said side sections to permit said comfort pads to rotate during placement of said collar about said patient to create a comfortable and secure fit and wherein said superstructure is a single unit comprised of a radiolucent plastic foam material.

* * * * *